(12) United States Patent
Chung

(10) Patent No.: US 6,943,278 B2
(45) Date of Patent: Sep. 13, 2005

(54) **TRANSGENIC *DROSOPHILA* HAVING A DISRUPTED *PARKIN* GENE AND EXHIBITS REDUCED CLIMBING ABILITY**

(75) Inventor: Jongkyeong Chung, Yusong-Gu Taejon (KR)

(73) Assignee: GenExel, Inc., Daejeon (KR)

(*) Notice: Subject to any disclaimer, the term of this patent is extended or adjusted under 35 U.S.C. 154(b) by 188 days.

(21) Appl. No.: 10/271,638

(22) Filed: Oct. 15, 2002

(65) Prior Publication Data

US 2004/0073955 A1 Apr. 15, 2004

(51) Int. Cl.[7] ...................... A01K 67/00; A01K 67/027; G01N 33/00
(52) U.S. Cl. ................................ 800/13; 800/3; 800/12
(58) Field of Search ................................. 800/3, 12, 13

(56) References Cited

FOREIGN PATENT DOCUMENTS

EP          1081225 A   *   3/2001   ........... C12N/15/12

OTHER PUBLICATIONS

Le Bourg et al. Hyypergravity, Aging and Longevity in *Drosophila melanogaster*. Comp. Biochem. Physiol. 1993, vol. 105A, No. 3, pp. 389–396.*
Giasson and Lee, Neuron 31:885 (2001).
Dawson, Cell 101:115 (2000).
Feany and Bender, Nature 404:394 (2000).
Muqit and Feany, Nat. Rev. Neurosci., 3:237 (2002).
Beal, Nat. Rev. Neurosci., 2:325 (2001).
Auluck et al., Science 295:865 (2002).

* cited by examiner

Primary Examiner—Deborah Crouch
(74) Attorney, Agent, or Firm—Medlen & Carroll, LLP

(57) ABSTRACT

The present invention relates to animal models for neuronal function, e.g., spontaneous changes in motor ability related to neuronal degeneration. For example, the present invention provides a *Drosophila melanogaster* model for Parkinson's disease. The present invention also provides methods for generating genetically based neuronal disease models, identifying genes that affect neuronal function and methods for identifying compounds having activity with respect to neurological function.

3 Claims, No Drawings

TRANSGENIC DROSOPHILA HAVING A DISRUPTED PARKIN GENE AND EXHIBITS REDUCED CLIMBING ABILITY

FIELD OF THE INVENTION

The present invention relates to animal models for neuronal function, e.g., spontaneous changes in motor ability related to neuronal degeneration. For example, the present invention provides a Drosophila melanogaster model for Parkinson's disease. The present invention also provides methods for generating genetically based neuronal disease models, identifying genes that affect neuronal function and methods for identifying compounds having activity with respect to neurological function.

BACKGROUND OF THE INVENTION

Parkinson's Disease (hereafter referred to as PD) is the second-most common progressive neurodegenerative disorder, affecting 1% of the population above the age of 65 (Beal, Nat. Rev. Neurosci., 2:325 (2001)) and over 4% by the age of 85 (Giasson and Lee, Neuron 31:885 (2001)). This disease is clinically characterized by slowed movement, resting tremor, rigidity, and postural instability (Beal, 2001). Its characteristic pathologies are the selective degeneration of dopamine-containing neurons in a region of the midbrain (the substantia nigra pars compacta), the formation of cytoplasmic accumulations of aggregated proteins called Lewy bodies (hereafter referred to as LB), and dystrophic neurites (Lewy neurites)(Beal 2001; Giasson and Lee, 2001). There is no proven preventative, restorative, or regenerative therapy for PD, and patients ultimately become quite disabled as a result of this disease (Dawson, Cell 101:115 (2000)).

Because many of the fundamental mechanisms that underlie neuronal death in PD remain unknown, developing suitable methods for studying PD has been difficult. Most cases of PD are sporadic, although specific genetic defects have been identified in several families with rare, inherited forms of the disease (Dawson, 2000). Both environmental and genetic factors are known to play roles in its progression, including oxidative stress and mitochondrial dysfunction, and the genes α-*synuclein, parkin,* and *ubiquitin carboxy-terminal hydrolase L1* (*UCHL*-1)(Giasson and Lee, 2001).

Recently numerous genes were identified by linkage analysis to rare familial forms of Parkinson's disease. Specifically identified were parkin, alpha-synuclein, and ubiquitin-C-hydrolase-L1 reviewed by Lansbury and Brice, 2002. Thus it is important to understand how genes are associated with loss of neurological function. There is a need to identify the nucleic acids and the functional parts of proteins that cause and modify PD-related symptoms. Thus, there is a need for models that facilitate the discovery and evaluation of therapeutic compositions for predicting, preventing, slowing, and reversing PD. Furthermore, genes that influence PD-related symptoms might vary in sequence among humans, and some variants may increase the predisposition for developing PD and exuberating symptoms. It would also be advantageous to provide a method for detecting an individual's predisposition to PD in order to prevent this condition.

SUMMARY OF THE INVENTION

The present invention relates to transgenic animals and methods of using transgenic animals. In some embodiments, the transgenic animals are invertebrate transgenic animals, particularly members of the phylum arthropoda, and more particularly members of the class insecta. In preferred embodiments, the models are transgenic flies. In many preferred embodiments, the transgenic flies are members of the family Drosophilidae (e.g., *Drosophila melanogaster*). The subject invention is further described in terms of transgenic flies employed at any stage of their life, e.g. in the egg stage, in the larval stage, in the adult stage, etc.

In preferred embodiments, the present invention relates to transgenic animal models for neuronal function, in particular to a spontaneously progressive loss of motor function. This loss of motor function is observed in adult transgenic flies described in the examples herein. This invention provides transgenic animals with disruptions within the parkin gene causing a loss of functional Parkin protein. In a preferred embodiment, the loss of functional Parkin is the result of knockout or loss of function of the Parkin protein.

The present invention provides methods for using transgenic animals in order to generate genetically based animal models. The present invention also provides methods for identifying genetic modifiers of neuronal function (e.g. proteins that directly or indirectly interact with Parkin), provides methods for identifying compositions that affect neuronal function (e.g. compounds that prevent, inhibit or restore neuronal degeneration) and provides methods of treatment.

Accordingly, in some embodiments, the present invention provides animals with transgenic somatic and germ cells having a functional disruption of at least one, and more preferably both, alleles of an endogenous parkin gene. Accordingly, the invention provides adult viable animals having a mutated, truncated, partially deleted or fully deleted, or disrupted parkin gene, with reduced (e.g., eliminated) Parkin protein production and/or activity. For embodiments of the present invention employing fly animal models, these animals are characterized by a spontaneous reduction in motor activity within 3–4 days of emerging from pupal cases. Loss of motor activity includes a reduction in walking and climbing activity. Pathologically these animals show neurodegeneration, including loss of dopaminergic neurons and loss of tyrosine hydroxylase enzyme.

Any method for using transgenic animals to generate models and methods for genetic screening and drug screening is contemplated by the present invention. In some embodiments, the parkin gene is preferably disrupted by genetic combinations with an endogenous wild-type parkin allele or mutant parkin gene that is present in an embryonic stem cell precursor of the animal. In additional embodiments, the parkin gene is preferably disrupted or compensated for by genetic combinations with an endogenous wild-type gene or appropriate sequence that would delete or restore the endogenous allele, or portion thereof, that has been introduced into an embryonic stem cell precursor of the animal. The embryonic stem cell precursor is then allowed to develop, resulting in an animal having a functionally disrupted or partially or fully restored motor activity. The animal may have one parkin gene allele functionally disrupted (i.e., the animal may be heterozygous for the null mutation), or more preferably, the animal has both parkin gene alleles functionally disrupted (i.e., the animal can be homozygous for the mutation).

In one embodiment of the invention, functional disruption of both parkin gene alleles produces animals in which expression of the parkin gene product in cells of the animal is substantially or completely absent relative to non-mutant animals. In another embodiment, the parkin gene alleles are disrupted such that an altered (i.e., mutant) parkin gene product is produced in cells of the animal. A preferred animal of the invention having a functionally disrupted parkin gene is a fly.

In some embodiments, the neurodegeneration is modified by genetic components. In some embodiments, the motor function is modified by genetic components.

In some embodiments, motor function is restored through compensation by genetic combinations with modifying genes. In some embodiments, neurodegeneration is abrogated through compensation by genetic combinations with modifying genes.

In some embodiments, the neurodegeneration is modified by compositions (e.g., drugs). In some embodiments, the motor function is modified by compositions (e.g., drugs).

The benefits of using a Drosophila animal model system in some preferred embodiments of the present invention have been exploited by the present invention to study PD. This PD model has tremendous utility in identifying PD causing genes, modifier genes of PD-related symptoms and therapeutic compounds.

The present invention also contemplates transgenic animals comprising parkin nucleic acids (i.e. the "transgene") or portions thereof. In a particular embodiment, transgenic animal of the present invention may be generated with the transgene contained in an inducible, tissue-specific promoter.

The present invention also finds use to identify new homologs of Parkin or natural mutations thereof. The present invention contemplates screening for homologs using standard molecular procedures.

Compounds or expression of nucleic acids that modify PD-related symptoms in Drosophila are also expected to affect PD-related symptoms in humans. A therapeutic method for treating PD may comprise the expression of a nucleic acid, its human homolog(s), or their encoded proteins. In another embodiment, a therapeutic method for treating PD may comprise a substantially purified protein, either recombinant or from a naturally occurring source, encoded by a nucleic acid or its human homolog(s). In yet another embodiment, compounds that affect the activity of the proteins encoded by a nucleic acid or its human homolog(s) may also comprise a therapeutic method for treating PD. In yet another embodiment, antibodies that bind to and affect the activity of the proteins encoded by a nucleic acid or its human homolog(s) may also comprise a therapeutic method for treating PD.

The present invention also provides a method for screening a compound library for compounds that modulate PD-related symptoms. This method comprises providing: i) an animal model; and ii) one or more test compounds; combining in any order, the animal model and one or more test compounds under conditions such that the animal model and the test compound interact; and detecting PD-related symptoms. In some embodiments, test compounds identified as modulating (e.g., improving) a symptom associated with PD are administered and/or tested in other mammals (e.g., humans) to determine the presence of or elicit a biological response. In some embodiments, the test compounds or sold and/or advertised for use as modulators or potential modulators of the symptom (e.g., for research or therapeutic use).

In some embodiments the present invention also relates to the use of nucleic acids of the present invention as diagnostic reagents. Variants of the gene characterized by the nucleic acid(s) of the human homolog(s) of nucleic acids that modify PD-related symptoms in the animal model might differentially predispose humans to developing PD. The detection of variants of the genes characterized by the nucleic acid that are associated with an individual's risk for developing PD provides a diagnostic tool that can add to, or define, a diagnosis of PD, or susceptibility to PD. In another embodiment, pre-existing therapeutic methods for treating PD exhibit varying efficacies due to variations in the gene(s) characterized by the human homolog(s) of the a nucleic acid within an individual's genome. The detection of these variants allows the most effective therapeutic method to be chosen. Detection of variants of the gene(s) characterized by the human homolog(s) of a PD-related symptom-modifying nucleic acid may be detected at the DNA level by a variety of techniques. Such methods comprise: providing nucleic acid from a subject; wherein the nucleic acid comprises a genetic allele; and detecting a variation in the nucleic acid, wherein the variant results in PD or predisposition to developing PD. In some embodiments, the mutation is in said gene variant. In some embodiments, the detecting step is accomplished by hybridization analysis. In some embodiments, the method further includes the step of providing a prognosis to the subject based on the presence or absence of the mutation. In some embodiments the method includes determining the functional capability of a PD associated protein.

GENERAL DESCRIPTION OF THE INVENTION

Both genetic factors and environmental conditions are known to play roles in the progression of Parkinson's disease. These include oxidative stress, mitochondrial dysfunction, and the genes parkin, α-*synuclein*, and *ubiquitin carboxy-terminal hydrolase L1* (*UCHL*-1) (Giasson and Lee, Neuron 31:885 (2001)).

Although it is not clear how the known PD genes might relate to each other in contributing to the disease pathology, the observation that the Parkin and α-synuclein proteins co-localize within LB has prompted several models based on these 2 proteins (Giasson and Lee, 2001). One compelling model is that functional Parkin is sequestered by an accumulation of α-synuclein, thus disabling protein degradation machinery required for proper cell function. Without sufficient protein degradation, cytotoxicity may occur due to the accumulation of unfolded proteins, and in fact might be exacerbated in neurons that are intrinsically exposed to oxidative stress. Therefore, methods of treatment for PD might involve the restoration of appropriate Parkin activity in order to reduce the accumulation of unfolded proteins or the prevention of α-synuclein aggregation.

The parkin gene encodes a protein that resembles ubiquitin and appears to act as an E3 ligase, a critical component of the ubiquitination pathway. In fact the ubiquitin protein degradation pathway appears to be involved in PD (Giasson and Lee, 2001). Furthermore, UCHL-1 encodes an enzyme involved in ubiquitin metabolism (Dawson, 2000; Giasson and Lee, 2001).

Rare missense mutations in α-synuclein are associated with autososmal dominant PD in a few families of European origin, and α-synuclein protein is a major component of LB and neurites (Dawson, 2000). α-synuclein can self-aggregate and assemble into fibrils that constitute the Lewy pathology (Dawson, 2001). Furthermore, its over-expression in several animal models recapitulates many of the important aspects of PD pathogenesis (Feany and Bender, Nature 404:394 (2000); Beal, 2001; Muqit and Feany, Nat. Rev. Neurosci., 3:237 (2002)).

Recently, a Drosophila model for PD has been generated using ectopic expression of human alpha-synuclein (Feany and Bender, 2000). Flies expressing alpha-synuclein in their nervous system display several PD-like phenotypes. Most interestingly, the dopaminergic neurons of the model flies were degenerated in an age-dependent manner. Consequently, the model flies were defective in locomotion at late adult stages. In addition, alpha-synuclein-immunoreactive cytoplasmic inclusions resembling LB were observed in the brains of the model flies. Using this model, it has been demonstrated that molecular chaperone hsp70 prevented dopaminergic neuronal loss associated with alpha-synuclein overexpression in Drosophila (Auluck et al., Science 295:865 (2002)). Despite recent progress in understanding the cellular function of Parkin, an in vivo model for Parkin that can be used as a disease model (e.g., a model that has a detectable phenotype) for PD has not been developed.

DEFINITIONS

To facilitate understanding of the invention, a number of terms are defined below.

As used herein, the term "animal" refers to any animal (e.g., a mammal), including, but not limited to, humans, non-human primates, rodents (e.g., mice, rats, etc.), flies, and the like.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5" and 3" ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (including heteronuclear RNA; hnRNA and mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5" ends" and "3" ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5" end" if its 5' phosphate is not linked to the 3' oxygen of a mononucleotide pentose ring and as the "3" end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region can comprise of cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complimentarily between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, slot blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization*[1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand. Regions of a nucleic acid sequences that are accessible to antisense molecules can be determined using available computer analysis methods.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a gene includes, by way of example, such nucleic acid in cells ordinarily expressing the gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. Coding regions in eucaryotes are a composion comprising of 5' ends with nucleotide triplets "ATG" that encode methionine and 3' end sequences comprising of nucleotide triplets that specify stop codons (eg., TAA, TAG, TGA).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the desired target. The removal of non-immunoglobulin proteins and/or the removal of immunoglobulins that do not bind to the intended target results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or one-, two- or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. Vector can include partial genes, gene fragments, full length genes and target sequences. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells utilize promoters, enhancers, and termination and polyadenylation signals.

As used herein, the term host cell refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed, often referred to as "housekeeping" genes (e.g., the amount of 28S rRNA, an abundant RNA transcript present at essentially the same amount in all tissues, present in each sample can be used as a means of normalizing or standardizing the mRNA-specific signal observed on Northern blots).

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has integrated foreign DNA into its genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for up to several cell divisions. During this time the foreign DNA is subject to the regulatory controls that govern the expression of endogenous genes in the chromosomes.

The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise cell lysate, a cell, a portion of a tissue, tissue lysate, whole flies, whole fly extract containing one or more proteins and the like.

DETAILED DESCRIPTION OF THE INVENTION

The present invention provides transgenic animals that exhibit a spontaneous motor degeneration, having somatic and/or germ cells in which at least one allele of an endogenous Parkin gene is functionally disrupted. The present invention provides assays for the detection of mutant Parkin genes and modifying genes associated with Parkinson's disease. The present invention also provides drug-screening assays.

Transgenic Animals Lacking Functional Parkin Genes and Homologs, Mutants, and Variants Thereof Preferred embodiments of the present invention are illustrated below using the example of a Drosophila model for mutant Parkin. It is understood that other non-human animals may be generated using methods known in the art. Parkin target sequences for disruption from various non-human animals (e.g., mice, rats) are readily identified from public sequence databases.

The animal may be heterozygous or, more preferably, homozygous for the Parkin gene disruption. As used herein, the term "gene disruption" refers to any genetic alteration that prevents normal production of Parkin protein (e.g., prevents expression of a Parkin gene product, expression of normal Parkin gene product, or prevents expression of normal amounts of the Parkin gene product). In some embodiments, the gene disruption comprises a deletion of all or a portion of the Parkin gene. In other embodiments, the gene disruption comprises an insertion or other mutation of the Parkin gene. In still other embodiments, the gene disruption is a genetic alteration that prevents expression, processing, or translation of the Parkin gene. In one embodiment, both Parkin gene alleles are functionally disrupted such that expression of the Parkin gene product is substantially reduced or absent in cells of the animal. The term "substantially reduced or absent" is intended to mean that essentially undetectable amounts of normal Parkin gene product are produced in cells of the animal. This type of mutation is also referred to as a "null mutation" and an animal carrying such a null mutation is also referred to as a "knockout animal." In preferred embodiments, the transgenic animals display a Parkinson's disease phenotype similar to that observed in humans.

A preferred embodiment of the present invention is based upon a non-mammalian animal model for PD in the fruit fly *Drosophila melanogaster* (hereafter referred to as Drosophila). One of the most profound and surprising biological discoveries in the last two decades is that most animals across the animal kingdom, including humans, possess many of the same genes that function in similar ways in cells, tissues and organs. In fact, only 94 of an estimated 1,278 human gene families are vertebrate-specific. Furthermore, at least 77% of known human disease genes have at least one counterpart within the genome of Drosophila, a model organism and workhorse in the study of genetics (Reiter et al., Gen. Res. 111:1114 (2001); Table 1). Many genes implicated in human diseases, including signaling pathways and effectors of tissue- and cell-specification, were originally identified and characterized in the fruit fly. Thus, genes within most human disease-associated networks are present in the fruit fly genome and have comparable roles in fly biology.

TABLE 1

Drosophila shares many important aspects of biology and disease pathways with humans

| Genes shared between humans & Drosophila | Human disease relevance |
| --- | --- |
| Signaling pathway | |
| Notch, presenilin, APP | Alzheimer's disease; leukemia |
| Hedgehog, ptc | Basal cell carcinoma; medulloblastoma |
| Insulins, InR, P13K, PDK | Diabetes |
| TGF-beta, Wnt | Colon cancer |
| G-protein coupled receptors | Obesity/diabetes; hypertension |
| Tissue formation | |
| SREBP, PPAR-gamma | Obesity/diabetes |

TABLE 1-continued

Drosophila shares many important aspects of biology and disease pathways with humans

| Genes shared between humans & Drosophila | Human disease relevance |
| --- | --- |
| MyoD, Mef | Muscular dystrophy; cardiomyopathy |
| Pax-6 | Aniridia |
| Cell structural/biological components | |
| p53, Akt, Rb, Abl, EGF-R | Transformation & malignancy |
| KCNQ1, KCNH2, SCN5A KCNQ3, BFNC2, EBN1, KCNQ2 | Long-QT syndrome Neonatal epilepsy |
| PKD1 | Polycystic kidney disease |
| Alpha-syn, parkin, UCHL-1 | PD |

These striking parallels in biological processes among animals are reflected in commercial applications for methods of treatment for human conditions. For example, the protein products of the Transforming Growth Factor-beta (TGF-beta) gene family act as for signaling molecules and regulate diverse biological activities (Hogan, Curr. Op. Gen. Dev. 6:432 (1996)). One subset of this family, the Bone Morphogenetic Proteins (BMPs), is characterized by its ability to induce bone formation, both when added to or expressed in cultured cells and when implanted in animals (Sampath et al., Roc. Natl. Acad. Sci. USA 90:6004 (1993)). This has been exploited in a medical device (FDA ref. no. H010002) in which the BMP protein OP-I is indicated for use as an alternative to autograft in recalcitrant long bone nonunions. The Drosophila counterpart of the OP-1 protein, called 60A, exhibits a very similar biological activity in rats and is sufficient to induce bone formation within dose ranges that have been reported for OP-I (Sampath et al., 1993). It is therefore expected that Drosophila nucleic acids, their encoded proteins, and the networks within which they interact will have biological activities almost identical to their human homologs. Hence, it is advantageous to use the strengths of Drosophila as an experimental system to study human diseases.

Utlilizing Transgenic Animals for Genetic Screens

In some embodiments, the Parkin animals of the present invention are crossed with other transgenic models or other stains of animals to generate F1 hybrids for additional disease models. In another embodiment, a disease condition is induced by breeding an animal of the invention with another animal genetically prone to a particular disease. For example, in some embodiments, the Parkin animal is crossed with knockout animals models of other genes associated with PD or related conditions.

In some embodiments, the Parkin animals are used to generate animals with an active Parkin gene from another species (a "heterologous" Parkin gene). In preferred embodiments, the gene from another species is a human gene. In some embodiments, the human gene is transiently expressed. In other embodiments, the human gene is stably expressed (e.g., the Parkin null animals are used to generate animals that are transgenic for human Parkin). Such animals find use to identify agents that inhibit human Parkin in vivo. For example, a stimulus that induces production of Parkin is administered to the animal in the presence and absence of an agent to be tested and the response in the animal is measured. An agent that inhibits human Parkin in vivo is identified based upon a decreased response in the presence of the agent compared to the response in the absence of the agent.

Identification of Binding Partners and Genetic Assays

In some embodiments, binding partners of Parkin amino acids are identified. In some embodiments, the Parkin nucleic acid or fragments thereof are used in fly two-hybrid screening assays and yeast two-hybrid screening assays. For example, in some embodiments, the nucleic acid sequences are subcloned into pGPT9 (Clontech, La Jolla, Calif.) to be used as a bait in a yeast-2-hybrid screen for protein-protein interaction of a human fetal kidney cDNA library (Fields and Song Nature 340:245, (1989); herein incorporated by reference). In other embodiments, phage display is used to identify binding partners (Parmley and Smith Gene 73 : 305, (1988); herein incorporated by reference). Binding partners identified by in vitro methods may be expressed (e.g., overexpressed) or regulated in the animals models of the present invention, in vivo, to identify biological effects in the context of the parkin animal model.

Drug Screening

The present invention provides methods and compositions for using transgenic animals as a target for screening drugs that can alter, for example, interaction between Parkin and binding partners (e.g., those identified using the above methods). Drugs or other agents (e.g., from compound libraries) are exposed to the transgenic animal model and changes in phenotypes or biological markers are observed or identified. For example, drugs are tested for the ability to improve neurological function or phenotypes associated with loss of neurological function.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994])); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Therapeutic Agents

The present invention further provides agents identified by the above-described screening assays. Accordingly, it is within the scope of this invention to further use an agent identified as described herein (e.g., Parkin transgenic knockout animal, hybrid of a Parkin transgenic knockout animal, progeny of Parkin transgenic knockout animal, neuronal modulating agent or Parkin mimetic, a Parkin specific antibody, or a Parkin-binding partner) in an appropriate animal model (such as those described herein) to determine the efficacy, toxicity, side effects, or mechanism of action, of treatment with such an agent. Furthermore, agents identified by the above-described screening assays can be used for treatments of neurologically related disease (e.g., including, but not limited to, Parkinson's disease).

EXPERIMENTAL

The following examples are provided in order to demonstrate and further illustrate certain preferred embodiments and aspects of the present invention and are not to be construed as limiting the scope thereof.

Example 1

Transgenic Model

A non-mammalian animal model for PD recapitulates many important aspects of human PD-related symptoms dparkin Gene The parkin gene was isolated in Drosophila, using the polymerase chain reaction (PCR) to amplify a region corresponding to the predicted open reading frame CG10523 whose sequence was obtained from the website hosted by the Berkeley Drosophila Genome Project. 1 μL of a Drosophila adult head cDNA library (Clontech) was used as a template in PCR reactions using the common 5' primer 5'-CGGGATCCATGAGTTTTATTTTTAAATTTATTG-3' (SEQ ID NO:1) and the 3' primer 5'-CCGCTCGAGTTAGCCGAACCAGTGGGCTCCC-3' (SEQ ID NO:2). For the PCR reaction, denaturation was carried out at 94° C. for 1 min, annealing at 55° C. for 1 min, and extension at 72° C. for 1 min. 35 amplication cycles were performed in Perkin Elmer thermal cycler. The sequence of this PCR product was consistent with the open reading frame deduced from a cDNA clone, SD01679, whose sequence was also obtained from the website hosted by Berkeley Drosophila Genome Project and was isolated as part of a high-throughput process to sequence clones from Drosophila Gene Collection 1 (Rubin et al., Science 287:2204 (2000)). The open reading frame encodes a 482 amino acid protein that has an estimated molecular weight of approximately 52 kDa. The conceptually translated Drosophila Parkin showed overall 58% similarity with its human orthologue, and has all the characteristic canonical motifs of vertebrate Parkin. Like its mammalian counterpart, Drosophila Parkin contains a ubiquitin-like domain (Ubl), two Ring finger domains, and an In Between Ring domain. In addition, Drosophila Parkin has a well-conserved putative caspase cleavage site, Asp 149. All these protein domains are known to those skilled in the art.

Consistent with the sequencing result, an approximately 1.5 kb-transcript of Drosophila parkin was detected by Northern blot analyses. This was done by preparing developmentally staged total RNAs using the easy-Blue™ system (Intron, Korea), and mRNAs were further purified using the Oligotex mRNA midi kit (Qiagen). Either 2 or 10 μg of mRNA per lane was separated by electrophoresis on denaturing formaldehyde agarose gels in MOPS buffer, transferred onto a nylon membrane, and successively hybridized with a nick-translated $^{32}$P-labeled Dpark 3' (Sambrook et al., Molecular Cloning: A Laboratory Manual, $3^{rd}$ edition, Cold Spring Harbor, N.Y.: Cold Spring Harbor Laboratory Press (1989)). Hybridized probes were visualized by autoradiography (Sambrook et al., 1989). The Drosophila parkin gene was highly expressed in adult and embryo stages. In adult flies, the Dparkin transcript was more strongly expressed in the head compared to the rest of the body.

Allelic dParkin Mutants and Relevance to Human PD

Two allelic mutants for Drosophila parkin (named Dpark[1] and Dpark[2]) were isolated from a large-scale EP-element mutagenesis screening (Rorth et al., Development 125:1049

(1998)). parkin mutants were selected by PCR-based screen with a Parkin 3' end primer (5'-TTAGCCGAACCAGTGGGCTCCCATGCAG-3' SEQ ID NO:3) and a P-element inverted terminal repeat primer (5'-ACCACCTTATGTTATTTCATCATG-3' SEQ ID NO:4). To detect the mutant lines in which a P-element is inserted in the Drosophila parkin gene, genomic DNA was extracted from all the candidate flies using Wizard genomic DNA purification kit (Promega) as recommended by the manufacturer, and PCR reactions were carried out using 1 μL of the genomic DNA as a template. For the PCR reaction, denaturation was carried out at 94° C. for 1 min, annealing at 55° C. for 1 min, and extension at 72° C. for 3 min. 35 amplication cycles were performed in Perkin Elimer thermal cycler using Taq polymerase (Takara). The insertion sites of P-element in Dpark$^1$ and Dpark$^2$ are located at basepairs +988 (the fourth exon) and +433 (the third exon) of the parkin open reading frame (ORF), designated AY093423 in the GenBank database at the National Center for Biotechnology Information, respectively. Both mutants contain an insertion of EP-element in exons. The effect of the P-element insertion on Drosophila parkin gene expression was determined in Dpark$^1$ homozygotes by Northern blot analyses using a probe derived from 3' end of the parkin open reading frame (base pairs +1016 to +1449 of the parkin ORF). Compared to the wild type control, Dpark$^1$ homozygous flies fail to express the intact parkin transcript.

In addition, new mutant parkin alleles were generated by transposase-induced excision of the P-element in Dpark$^1$ flies using delta-2-3 transposase using the method of Robertson et al. (Genetic 118:461 (1988)), a method familiar to those skilled in the art. Precise excision of the P-element generated 10 revertant lines that produced the normal parkin mRNA, indicating that the loss of parkin mRNA expression in Dpark$^1$ mutant was indeed caused by the P-element insertion. However, other 30 independent lines (including the allele Dpark 68) from the same P-element excision experiment showed a complete loss of Drosophila parkin mRNA expression, which was tested by the RT-PCR. These analyses entailed using 1 μg of total RNAs as a template. First strand synthesis was achieved with MMLV reverse transcriptase (Promega, Wis.), and 1 μL of this RT product was used in a 50 μL PCR reaction with Taq polymerase (Takara) using Drosophila parkin-specific primers (5' primer: 5'-CGCCACCGAGGAGTATGTCCTACAGG-3' (SEQ ID NO:5), 3' primer: 5'-TTAGCCGAACCAGTGGGCTCCCATGCAG-3' (SEQ ID NO:6)). For the PCR reaction, denaturation was carried out at 94° C. for 1 min, and annealing at 55° C. for 1 min, and extension at 72° C. for 1 min. 35 amplification cycles were performed in Perkin Elimer thermal cycler. Next, the PCR products were sequenced using the Sp1 primer (5'-ACA CAA CCT TTC CTC TCA ACA A-3' (SEQ ID NO:7)) and the ABI BigDye Terminator Cycle Sequencing Ready Reaction Kit (Perkin Perkin-Elmer/Applied Biosystems), and run on an ABI 377XL Automated Sequencer (Perkin Perkin-Elmer/Applied Biosystems) in polymerized Long Ranger Gel Solution (FMC Bioproducts). PCR-based molecular analyses confirmed that most of the exons in the parkin gene had been deleted.

The distribution of the parkin transcripts in embryos and adult brains were examined by RNA in situ hybridization. In situ hybridizations of whole-mount embryos were performed with single-stranded digoxigenin-labeled RNA probes as described (Cho et al., Proc. Natl. Acad. Sci. USA 98:6144 (2001)) in a manner familiar to those skilled in the art. Dpark 3' probe DNA, which was also used for the Northern blot probe, was used as a template for making the RNA probe. Control probes for the antisense strand gave no specific signals. In wild type embryos, the parkin transcript was detected in the central nervous system (CNS), implying that parkin might play a role in the CNS in the embryo. However, no hybridization signals were detected in Dpark$^1$ embryos with the parkin anti-sense RNA probe or wild type embryos with the parkin sense RNA probe. parkin gene expression was also observed in wild type or Dpark$^1$ adult brains. This was done by collecting severed Drosophila heads at 1, 15, and 30 days after eclosion (herein referred to as days after emerging from the pupal case), fixing them with 4% paraformaldehyde and embedding them in paraffin. Serial brain sections with 5 μm intervals were prepared from the paraffin embedded samples using a microtome (Leica) and stored at 4° C., as previously described (Feany and Bender, 2000). The parkin transcripts were detected from most of the surrounding cell bodies throughout the brain, and highly enriched in those cell bodies located in the dorso medial (DM) region of hemisphere. However, no signals were detected in any Dpark$^1$ brains.

parkin mutant flies older than 3-4 days after eclosion moved extremely slowly or not at all, remaining on the bottom of the culture vials. To quantify the locomotor behavioral defects of parkin mutant flies, the climbing ability of the mutants was examined. To do so, fifteen flies were placed in a plastic vial, and gently tapped to the bottom of the vial. The number of flies at the top of the vial was counted after 18 seconds of climbing. Ten trials were performed for each time point. The trial numbers were then averaged, and the resulting mean was normalized by the mean value of 1-day-old wild type. These used as the climbing scores for each single group of flies on a particular day. The experiment was repeated five times, with independently derived transgenic lines. The climbing score for five repeated experiments was then averaged, and a group mean and standard error were obtained. As previously reported (Ganetzky and Flanagan, Exp. Gerontol., 13:189 (1978); Le Bourg and Lints, Gerontology 8:59 (1992); Feany and Bender, 2000; Pendleton et al., J. Pharmacol. Exp. Ther. 300:91 (2002)), wild type flies rapidly climb to the top of a vial when tapped to the bottom, and have a strong tendency to remain at the top. However, as the flies get older, they no longer climb to the top of the vial, in other words they lose climbing ability (Ganetzky and Flanagan, 1978; Le Bourg and Lints, 1992; Feany and Bender, 2000; Pendleton et al., 2002). The climbing abilities of all the parkin mutants were dramatically reduced to about 50%–60% of the wild type, even from the first day of eclosion, and their climbing abilities were completely lost at an age of approximately 30 days (5% in Dpark$^1$ and 4% in Dpark$^2$ at 24 days old). The preceding data are summarized in Table 2 below. In addition, transheterozygotes for Dpark$^1$ and Dpark$^2$ also showed defects in climbing ability (30.50±5.97% at 15 days old), while heterozygous Dpark$^1$ flies showed a normal climbing ability (86.30±3.41% at 15 days old).

TABLE 2

% climbing abilities of WT and parkin mutant flies at various time point over a 60 day period

| Age (days) | WT | Dpark$^1$/Dpark$^1$ | Dpark$^2$/Dpark$^2$ |
|---|---|---|---|
| 0 | 100 | 55.5 | 52.21 |
| 4 | 96.78 | 53.34 | 51.39 |
| 8 | 36.37 | 30.14 | 92.24 |

TABLE 2-continued

% climbing abilities of WT and parkin mutant flies at various time point over a 60 day period

| Age (days) | WT | Dpark[1]/Dpark[1] | Dpark[2]/Dpark[2] |
|---|---|---|---|
| 12 | 98.24 | 35.43 | 28.22 |
| 16 | 25.02 | 15.47 | 83.93 |
| 20 | 82.29 | 27.93 | 8.21 |
| 24 | 77.3 | 5.07 | 4.11 |
| 28 | 73.41 | 3.12 | 0 |
| 32 | 38.22 | 8.16 | 0 |
| 36 | 29.11 | 4.22 | 0 |
| 40 | 26.23 | 2.12 | 0 |
| 44 | 25.73 | 0 | 0 |
| 48 | 16.11 | 0 | 0 |
| 52 | 3.09 | 0 | 0 |
| 56 | 0.27 | 0 | 0 |
| 60 | 0 | 0 | 0 |

Adult fly brains were examined with immunohistochemical methods to look for any defects in dopaminergic neurons. Serial sections were made through the entire brain of the adult fly and immunostained with antibody against tyrosine hydroxylase (TH), which specifically identifies dopaminergic neurons in brains. This was done by fixing Drosophila heads collected from flies at 1, 15, and 30 days after eclosion with 4% paraformaldehyde and embedding them in paraffin. Serial brain sections with 5 μm intervals were prepared from the paraffin embedded samples using a microtome (Leica) and stored at 4° C., as previously described (Feany and Bender, 2000). Immunostaining on paraffin sections was performed by incubating sections in either rabbit anti-TH antibody (Pelfreeze) or sheep anti-TH antibody (Pelfreeze) overnight at a dilution of 1:100 in PBS. Sections were then washed 3 times in buffer and incubated in either horseradish peroxidase (HRP) (Amersham)- or fluorochrome-conjugated secondary antibodies (Sigma), described previously (Sullivan et al., 2000). Immunostained brain sections were viewed with light microscopes or laser scanning confocal microscopes (Zeiss, Germany). The brains of 1-day-old wild type flies had a normal complement of prominent dopaminergic neurons localized in the DM region in a symmetrical manner. The average number of TH-positive neurons in the DM region was about 15. In the parkin mutant, the number of TH-positive neurons was reduced to approximately two thirds of wild-type, even in 1-day-old fly brains. The TH-positive dopaminergic neurons were not lost in the wild-type aged fly brains, as they were readily identified even in 30-day-old flies. In contrast, parkin mutant flies aged for 15 days consistently exhibited a dramatic loss of TH-positive neurons in the DM region Example 2
The Drosophila Model for PD can be Used to Screen for Compounds that Affect PD-Related Symptoms A compound was screened for its ability to rescue the defective climbing response of Dpark[1] and Dpark[2] mutants. Flies were reared and crossed on Caltech medium (Ashbumer, Drosophila, Cold Spring Harbor, N.Y.: Cold Spring Harbor Laboratory Press (1989)) at 25° C. Wild type or parkin mutant flies were fed either L-DOPA or D-DOPA for 10 days by placing dry yeast that was soaked with 0.3 mL of either 1 mM L-DOPA or 1 mM D-DOPA on the bottom of the vial. Feeding 1 mM L-DOPA to Dpark[1] or Dpark[2] flies significantly restored the climbing response (up to almost 70% of the unfed wild type control) in these flies, while D-DOPA was not effective. Neither L-DOPA nor D-DOPA was effective on wild type flies. These data are summarized below in Table 3.

TABLE 3

% climbing abilities of WT and parkin mutant flies under no treatment, and treated with either D- or L-dopa

| Treatment | WT | Dpark1/Dpark1 | Dpark2/Dpark2 |
|---|---|---|---|
| None | 100.00 ± 2.29 | 36.17 ± 2.65 | 37.00 ± 3.49 |
| D-dopa | 101.90 ± 2.72 | 33.221 ± 1.87 | 37.75 ± 2.44 |
| L-dopa | 100.59 ± 2.73 | 68.20 ± 6.06 | 68.51 ± 10.09 |

Example 3
The Drosophila Model for PD can be Used in Genetic Modifier Screens to Discover Genes that act Within PD-Related Pathways The ability to ectopically express nucleic acids in a conditional, tissue-specific manner is an important tool in Drosophila biology. One method, used widely by those skilled in the art, is the Gal4-UAS system (Brand and Perrimon, Development 118:401 (1993)). Briefly, this system comprises genetically crossing two different transgenic Drosophila lines that carry transposable elements, called P-elements (U.S. Pat. No. 4,670,388, herein incorporated by reference in its entirety), within their genomes. A P-element insertion in one line contains a nucleic acid fragment encoding the yeast Gal4 transcriptional activator protein. Gal4 protein can be expressed either by an endogenous promoter in the Drosophila genome upstream of the insertion site of a P-element carrying the Gal4 open reading frame and a minimal promoter, or by a regulatory element that is engineered into the P-element upstream of the Gal4 open reading frame and a minimal promoter. In the former case Gal4 protein is expressed in the pattern of the endogenous enhancer, while in the latter, Gal4 protein is expressed in the pattern of the regulatory element placed upstream of it. The second transgenic Drosophila line carries a P-element containing a tandem array of fourteen upstream activation sequence (UAS) sites upstream of a nucleic acid encoding a gene of interest. One embodiment of this latter type of P-element that is commonly used by those skilled in the art has the UAS sites upstream of an hsp70 promoter and a multiple cloning site to facilitate the insertion of a gene of interest and is referred to as pUAST (Brand and Perrimon, 1993). A genetic cross of the two Drosophila lines results in the inheritance of both kinds of P-elements in a fraction of their progeny. In these progeny, the Gal4 protein is locally mis-expressed in some tissues, in which it binds to the UAS sites in the second P-element, resulting in expression of the gene of interest. This system exhibits a tremendous amount of flexibility in both the patterns of Gal4 expression lines available, and in being able to engineer pUAST constructs containing any gene of interest.

To screen for modifiers of PD-related symptoms, one uses a genetic screen. Genetic screens can be used to discover other genes that execute biological processes (St. Johnston, Nat. Rev. Gen., 3:176 (2002)). One method known to those skilled in the art employs a library of EP fly lines (Rorth et al., 1998). EP lines each contain a genomic insertion of a P-element that contains fourteen tandem copies of the upstream activator sequences (UAS) from yeast immediately upstream of a basal promoter. This sequence is bound with high affinity by the Gal4 transcriptional activator protein. The insertion of an EP element thus places a Gal4-inducible promoter either (1) near the 5' (upstream) end of a gene or; (2) places an inducible promoter within a gene. Wherever Gal4 protein is present within the fly, genes into which an EP element has inserted will either be (1) activated or; (2) inactivated via expression of an anti-sense RNA.

To identify genes that modify PD-related symptoms, PD model flies carrying in their genomes a dopaminergic neuron specific-inducible Gal4 driver (Dopadecarboxlase (Ddc)-Gal4) (Feany and Bender, 2000; Li et al., 2000) or various other Gal4 drivers, known to those skilled in the art, are crossed to independent EP lines. The eggs produced in these crosses are collected for 24 hours, and the behaviors and other phenotypes of adults are analyzed according to methods described in Example 2. EP lines are considered to have insertions into genes that modify the PD-related symptoms if there is a detectable increase or decrease in traits of Drosophila PD model flies containing both a Gal4 driver and an EP insertion compared to Drosophila PD model flies containing either Ddc-Gal4 or an EP element alone.

To determine the genomic regions into which the EP elements have inserted in each of the PD-related symptoms-modifying EP lines and thereby identify the causative open reading frames, DNA sequences flanking each EP element are recovered using inverse PCR on genomic DNA from each EP line according to the method by J. Rehm at the Berkeley Drosophila Genome Project website, which is very commonly utilized both those skilled in the art.

Briefly, for each EP fly line 15-20 frozen flies are completely macerated in 500 µL of grinding buffer (350 mM NaCl, 7M Urea, 100 mM Tris, 10 mM EDTA and 2% SDS), and proteins are removed by a phenol/chloroform extraction procedure. Genomic DNA is then precipitated with 100% ethanol, air-dried, and resuspended in 100 µL of TE buffer (10 mM Tris-Cl, 1 mM EDTA). Genomic DNA is then digested with HinPI endonuclease (MBI Fermentas) for 2 hrs at 37° C. and the residual enzyme activity subsequently heat inactivated. The digested DNA is then treated with T4 DNA ligase (MBI Fermentas) overnight at 4° C. The ligated DNA is recovered precipitated with isopropanol and sodium acetate (pH 5.2), and solubilized in 100 µL of TE (10 mM Tris-Cl, 1 mM EDTA). 10 µL of the ligated DNA is then amplified via PCR using primers 5R3 (5'-GCGAATCATTAAAGTGGGTATC-3' SEQ ID NO:8) and 5F3 (5'-GAGATGCATCTACACAAGGAAC-3' SEQ ID NO:9) that are targeted to the 5' region of EP element sequences. PCR products are purified via elution through a PCR purification column (Qiagen) with 50 µL of TE.

Secondary PCR reactions are then performed under cycling and buffer conditions described above using the 5R2 (5'-AATAGCACACTTCGGCAC-3' SEQ ID NO: 10) and 5F1 (5'-AATGAACCACTCGGAACC-3' SEQ ID NO:11) primers. As previously, the PCR products are then purified over a column and stored at −20° C.

The secondary PCR products from each of the EP lines are sequenced using the Spl primer (5'-ACA CAA CCT TTC CTC TCA ACA A-3' SEQ ID NO: 12) and the ABI BigDye Terminator Cycle Sequencing Ready Reaction Kit (Perkin Perkin-Elmer/Applied Biosystems), and run on an ABI 377XL Automated Sequencer (Perkin Perkin-Elmer/Applied Biosystems) in polymerized Long Ranger Gel Solution (FMC Bioproducts).

If at least 20 base pairs of flanking sequence are recovered from the cloned inverse PCR product from an EP insertion, the sequence is searched against all Drosophila sequences using the BLAST search tool, familiar to those skilled in art, at the Berkeley Drosophila Genome Project website, and matches are validated by their e-values, which establish the statistically significant threshold for reporting database sequence matches (Altschul, J. Mol. Evol. 36:290 (1993)). The scaffold of Drosophila genomic sequence that shows the highest sequence identity with each flanking DNA sequence is selected, and the exact position of the EP insertion relative to the flanking sequence is determined. Expressed sequence tags, complementary DNA's, and predicted open reading frames closest to the inserted EP element are searched for, and the direction of genes relative to the EP transcription unit (dictated by the direction of the EP promoter and UAS sites) is analyzed using databases in websites hosted by the National Center for Biotechnology Information and Berkeley Drosophila Genome Project. Candidate genes associated with an EP insertion and an open reading frame or an EST is identified as genes that modify PD-related symptoms.

Drosophila, human, mouse, and rat homologs of the PD-related symptoms-modifying genes are identified by inputting the amino acid sequences encoded by open reading frame sequences or ESTs associated with the Drosophila PD-related symptoms-modifying genes in blastp searches using the BLAST search tool of the National Center for Biotechnology Information. Drosophila, human, mouse, and rat proteins whose sequences match the Drosophila PD-related symptoms-modifier protein sequences with sufficiently-low e-values, and their encoding nucleic acids are also expected to modify PD-related symptoms.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A transgenic *Drosophila* whose genome comprises a homozygous or transheteroygous disruption in its endogenous *Parkin* gene, wherein said disruption reduces or eliminates the expression of functional *Parkin*, and said fly exhibits reduced climbing ability.

2. A method of screening a compound, comprising:
 a. Exposing the *Drosophila* of claim 1 to a test compound; and
 b. Determining an effect of said compound on the climbing ability of the *Drosophila* as campared to a *Drosophila* of claim 1 not exposed to said compound.

3. The method of claim 2, further comprising selecting the compound that improves climbing ability in the *Drosophila*.

* * * * *

SEQUENCE LISTING

<160> NUMBER OF SEQ ID NOS: 12

<210> SEQ ID NO 1
<211> LENGTH: 33
<212> TYPE: DNA
<213> ORGANISM: Artificial Sequence
<220> FEATURE:
<223> OTHER INFORMATION: Synthetic

<400> SEQUENCE: 1
cgggatccat gagttttatt tttaaattta ttg     33

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
ccgctcgagt tagccgaacc agtgggctcc c     31

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
ttagccgaac cagtgggctc ccatgcag     28

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
accaccttat gttatttcat catg     24

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
cgccaccgag gagtatgtcc tacagg     26

<210> SEQ ID NO 6
<211> LENGTH: 28
<212> TYPE: DNA
<213> ORGANISM: Artificial Sequence
<220> FEATURE:
<223> OTHER INFORMATION: Synthetic

<400> SEQUENCE: 6
ttagccgaac cagtgggctc ccatgcag     28

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
acacaacctt tcctctcaac aa     22

<210> SEQ ID NO 8
<211> LENGTH: 22
<212> TYPE: DNA

```
<213> ORGANISM: Artificial Sequence
<220> FEATURE:
<223> OTHER INFORMATION: Synthetic

<400> SEQUENCE: 8
gcgaatcatt aaagtgggta tc                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gagatgcatc tacacaagga ac                                              22

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
aatagcacac ttcggcac                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
aatgaaccac tcggaacc                                                   18

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
acacaacctt tcctctcaac aa                                              22
```